(12) United States Patent
Trout, III

(10) Patent No.: US 7,105,012 B2
(45) Date of Patent: Sep. 12, 2006

(54) POSITIONING ASSEMBLY AND METHOD OF USE

(75) Inventor: Hugh H. Trout, III, Washington, DC (US)

(73) Assignee: Eva Corporation, Bethesda, MD (US)

( * ) Notice: Subject to any disclaimer, the term of this patent is extended or adjusted under 35 U.S.C. 154(b) by 166 days.

(21) Appl. No.: 10/173,659

(22) Filed: Jun. 19, 2002

(65) Prior Publication Data

US 2002/0193821 A1  Dec. 19, 2002

Related U.S. Application Data

(60) Provisional application No. 60/298,896, filed on Jun. 19, 2001.

(51) Int. Cl.
*A61F 2/06*    (2006.01)
*A61B 1/32*    (2006.01)
*A61M 29/00*   (2006.01)

(52) U.S. Cl. ............... 623/1.11; 623/1.23; 600/207; 606/194; 604/101.01

(58) Field of Classification Search ............ 606/1, 606/108, 127, 190–200, 213; 600/201, 204, 600/207; 604/96.01–112; 623/1.1, 1.11
See application file for complete search history.

(56) References Cited

U.S. PATENT DOCUMENTS 5,087,265 A * 2/1992 Summers .............. 606/159
5,147,377 A * 9/1992 Sahota .................. 606/194
5,207,695 A * 5/1993 Trout, III ............... 623/1.36
5,527,325 A * 6/1996 Conley et al. ........... 606/159
5,569,296 A * 10/1996 Marin et al. ............ 606/198
5,669,924 A   9/1997 Shaknovich
5,690,668 A * 11/1997 Fogarty et al. .......... 606/192
5,921,958 A * 7/1999 Ressemann et al. ..... 604/96.01
6,123,712 A * 9/2000 Di Caprio et al. ........ 606/108
6,183,509 B1  2/2001 Dibie
6,379,365 B1 * 4/2002 Diaz .................... 606/108
6,506,180 B1 * 1/2003 Lary .................... 604/103.12
6,527,790 B1 * 3/2003 Chien et al. ............ 606/194
6,656,213 B1 * 12/2003 Solem .................. 623/1.11

FOREIGN PATENT DOCUMENTS

JP       2003250896   *  9/2003   ......... 604/103.05

* cited by examiner

*Primary Examiner*—Glenn K. Dawson
(74) *Attorney, Agent, or Firm*—John N. Coulby; Kelley Drye & Warren LLP

(57) ABSTRACT

The present invention is directed to a positioning apparatus for use during a surgical procedure, which may involve the repair of a vessel. The positioning apparatus in accordance with an embodiment of the present invention may comprise a delivery assembly and a distensible member having at least one expansible member. The expansible member has a distal end and a proximal end, wherein the proximal end is interposed with the delivery assembly. The positioning apparatus, by way of the at least one expansible member, is used to position an object within a vessel that may or may not be aneurismal.

9 Claims, 3 Drawing Sheets

POSITIONING ASSEMBLY AND METHOD OF USE

CROSS-REFERENCE TO RELATED APPLICATIONS

The present invention relates to, and is entitled to the benefit of the earlier filing date and priority of, U.S. Provisional Application Ser. No. 60/298,896, filed Jun. 19, 2001.

FIELD OF THE INVENTION

The present invention relates generally to a surgical positioning apparatus and method of use. In particular, the present invention relates to a distensible positioning apparatus for use in surgical procedures. More specifically, embodiments of the present invention are directed to a positioning apparatus for use in repairing a vessel during a surgical procedure.

BACKGROUND OF THE INVENTION

An aneurysm is a ballooning of the wall of an artery resulting from the weakening of the artery due to disease or other conditions. Left untreated, the aneurysm will frequently rupture, resulting in loss of blood through the rupture and death.

Aortic aneurysms are the most frequent form of arterial aneurysm and are life threatening. The aorta is the main artery, which supplies blood to the circulatory system. The aorta arises from the left ventricle of the heart, passes upward and bends over behind the heart, and passes down through the thorax and abdomen. Among other arterial vessels branching off the aorta along its path, the abdominal aorta supplies two side vessels to the kidneys, the renal arteries. Below the level of the renal arteries, the abdominal aorta continues to about the level of the fourth lumbar vertebrae (or the navel), where it divides into the iliac arteries. The iliac arteries, in turn, supply blood to the lower extremities and perineal region.

It is common for an aortic aneurysm to occur in that portion of the abdominal aorta between the renal arteries and the iliac arteries. This portion of the abdominal aorta is particularly susceptible to weakening, resulting in an aortic aneurysm. Such an aneurysm is often located near the iliac arteries. An aortic aneurysm larger than about 5 cm in diameter in this section of the aorta is ominous. Left untreated, the aneurysm may rupture, resulting in rapid, and usually fatal, hemorrhaging. Typically, a surgical procedure is not performed on aneurysms smaller than 5 cm because presently no statistical benefit exists in performing such procedures.

Aneurysms in the abdominal aorta are associated with a particularly high mortality rate; accordingly, current medical standards call for urgent operative repair. Abdominal surgery, however, results in substantial stress to the body. Although the mortality rate for an aortic aneurysm is extremely high, there is also considerable mortality and morbidity associated with open surgical intervention to repair an aortic aneurysm. This intervention involves penetrating the abdominal wall to the location of the aneurysm to reinforce or replace the diseased section of the aortic aneurysm. A prosthetic device, typically a synthetic tube graft, is used for this purpose. The graft serves to exclude the aneurysm from the circulatory system, thus relieving pressure and stress on the weakened section of the aorta at the aneurysm.

Repair of an aortic aneurysm by surgical means is a major operative procedure. Substantial morbidity accompanies the procedure, resulting in a protracted recovery period. Further, the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

In recent years, apparatus and methods have been developed attempting to treat an aortic aneurysm without the attendant risks of intra-abdominal surgical intervention. Among them are inventions disclosed and claimed to endovascular and endoluminal prosthetics. These prosthetics appear to be promising but are significantly restricted. Primarily, current prosthetics are limited by the prosthetic's degree of similarity to the diseased vascular or luminal vessel the prosthesis will replace. The size, location, position, and specific geometry of the aortic aneurysm, however, is dependent on an individual patient and very often, aortic aneurysms occur in close proximity to, if not along, lateral branching vessels. The specific geometry between the abdominal aorta and iliac arteries, and extent of disease infestation, and the integrity of the vessel wall are often determinant factors in the availability and use of known prosthetics.

Besides being able to accommodate size, location, position, and specific geometry of a patient's aneurysm, the prosthetic needs to be positioned appropriately within the vessel containing the aneurysm to a branch vessel for sealing purposes. In order to position the prosthetic graft to accommodate the branching vessels, the use of anchoring members, expandable support grafts, radially expandable regions, trunk sealing cuffs, and the use of hardening agents have tried solve this problem. The variability between patients, however, is a limiting factor.

Current mechanisms to solve the positioning problem fall short in adapting to the individual patient, which results in inefficient and ineffective prosthetics. Additionally to position the prosthetic graft, the graft may need to be moved anteriorly or posteriorly once inserted. Known positioning mechanisms fail to provide a way to allow for adjustment of the prosthetic graft around the branching vessel area. Similarly, known positioning mechanisms may require a short occlusion of blood flow, although the occlusion of blood flow results in irreparable damage to tissues and organs. Hence, although in recent years certain techniques have been developed that may reduce the stress, morbidity, and risk of mortality associated with surgical intervention to repair aortic aneurysms, none of the systems that have been developed effectively treat the aneurysm and exclude the affected section of aorta from the pressures and stresses associated with circulation.

What is needed, therefore, is a variable expansible member system that provides an adjustable surface to be moved and size to be increased or decreased wherein an object within a vessel can be maneuvered into a position where further manipulations of the object can be employed. Specifically, the variable expansible member system could be used to maneuver a prosthetic aortic graft anteriorly or posteriorly during a surgical procedure. The variable expansible member system may also be used, for example, to maneuver a prosthetic graft such that the graft can be attached around an orifice of a branching artery where flow is essential to the function of critical organs.

It is therefore an advantage of some, but not necessarily all, embodiments of the present invention to provide a variable expansible positioning apparatus for maneuvering an object within a vessel.

It is another advantage of embodiments of the present invention to provide an apparatus for maneuvering the position of a surgical component, such as a prosthetic graft, for attachment to a vessel wall.

It is yet another advantage of embodiments of the present invention to provide an apparatus for maneuvering a surgical component for attachment around an orifice of a branching artery.

It is another advantage of embodiments of the present invention to provide an apparatus for positioning a surgical component without occluding blood flow.

Additional advantages of various embodiments of the invention are set forth, in part, in the description that follows and, in part, will be apparent to one of ordinary skill in the art from the description and/or from the practice of the invention.

SUMMARY OF THE INVENTION

Responsive to the foregoing challenges, Applicant has developed an innovative positioning apparatus for use during a surgical procedure. According to an embodiment of the present invention, the positioning apparatus comprises: a delivery assembly; and a distensible member having at least one expansible member, the at least one expansible member having a distal end and a proximal end wherein the proximal end is interposed with the delivery assembly.

The at least one expansible member may be distended such that the expansible member abuts a surgical component for maneuvering the surgical component during the surgical procedure. The at least one expansible member may be interfaced with a surgical component during the surgical procedure. The at least one expansible member may be interfaced with the surgical component in the form of an interconnection.

The delivery assembly may further comprise a plurality of chambers and the proximal end of the at least one expansible member may be interposed with a chamber of the delivery assembly.

According to another embodiment of the present invention, the positioning apparatus for maneuvering a surgical component during a surgical procedure comprises: a delivery assembly; a distensible member having at least one expansible member, the at least one expansible member having a distal end and a proximal end wherein the proximal end is interposed with the delivery assembly; and wherein the at least one expansible member is distended such that the expansible member abuts the surgical component.

In this embodiment, the at least one expansible member may be interfaced with the surgical component during the surgical procedure. The at least one expansible member may be interfaced with the surgical component in the form of an interconnection. The delivery assembly may further comprise a plurality of chambers and the proximal end of the at least one expansible member may be interposed with a chamber of the delivery assembly.

According to another embodiment, the positioning apparatus for maneuvering a surgical component during a surgical procedure comprises: a delivery assembly having a plurality of chambers; a distensible member having a first and a second expansible member, the first expansible member having a distal end and a proximal end and a front and a back wherein the proximal end is interposed with a chamber of the delivery assembly and the back is abutted against a vessel wall, the second expansible member having a distal end and a proximal end and a front and a back wherein the proximal end is interposed with a chamber of the delivery assembly and the front is abutted against the surgical component; and wherein the first and second expansible members are distended.

In this embodiment, the second expansible member may be interfaced with the surgical component during the surgical procedure. The second expansible member may be interfaced with the surgical component in the form of an interconnection. Alternatively, the second expansible member may be interfaced with the surgical component in the form of a compression site. The first expansible member may be in contact with the second expansible member forming an interface. The interface may be flat, grooved, or an attachment.

The present invention is also directed to a method of positioning a surgical component, comprising the steps of: delivering a positioning apparatus to a surgical site; and distending at least one expansible member of the positioning apparatus such that the at least one expansible member abuts the surgical component for maneuvering the position of the surgical component. The step of distending the at least one expansible member may further comprise the step of distending the expansible member by an expansion element selected from the group consisting of: air, gas, and liquid.

The method may further comprise the step of urging the surgical component against a vessel wall. The method may further comprise the step of maneuvering the positioning of the surgical component anteriorly or posteriorly with the positioning apparatus. The method may further comprise the step of maneuvering the positioning of the surgical component with the positioning apparatus to align the surgical component with a vessel wall having an attachment of a branching artery. The method may further comprise the step of attaching the surgical component to the vessel wall around an orifice of the branching artery. The method may further comprise the step of varying the distension of the at least one expansible member of the positioning apparatus to further manipulate the surgical component.

It is to be understood that both the foregoing general description and the following detailed description are exemplary and explanatory only, and are not restrictive of the invention, as claimed. The accompanying drawings, which are incorporated herein by reference, and which constitute a part of this specification, illustrate certain embodiments of the invention and, together with the detailed description, serve to explain the principles of those embodiments of the present invention.

BRIEF DESCRIPTION OF THE DRAWINGS

In order to assist the understanding of this invention, reference will now be made to the appended drawings, in which like reference characters refer to like elements. The drawings are exemplary only, and should not be construed as limiting the invention.

DETAILED DESCRIPTION OF EMBODIMENTS OF THE INVENTION

Figure 1:
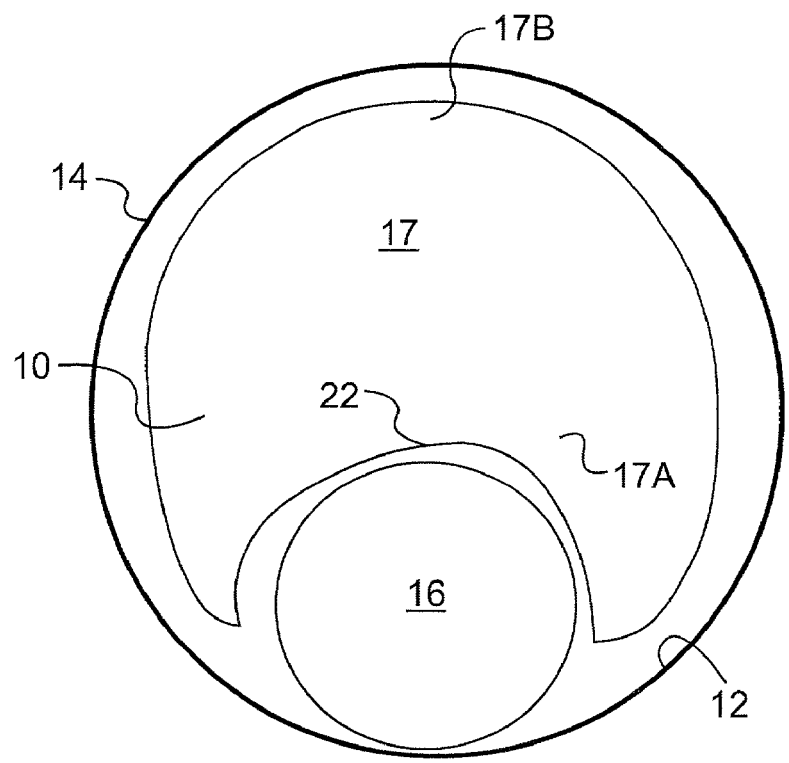
FIG. 1 is a transverse view of an embodiment of the present invention having a expansible member within a vessel.

An embodiment of the present invention will now be described in connection with the surgical repair of a vessel. The vessel may be involved in an aneurysm. The invention, however, is not limited solely to use in the repair of an aneurysm with a surgical component, such as, but not limited to, a prosthetic graft; rather, it is contemplated that the positioning apparatus according to the present invention may be used in other repairing surgical procedures.

A positioning apparatus 10 in accordance with embodiments of the present invention is disclosed in FIGS. 1, 2, 3, 4, and 5. In an embodiment demonstrated in FIG. 1, a positioning apparatus 10 comprises a delivery assembly (not illustrated in FIG. 1) and a distensible member 17. The delivery assembly may include, but is not limited to, a catheter, or any other suitable apparatus or method for delivery of a distensible member 17 to the site of the surgical procedure. The distensible member 17 may include, but is not limited to, at least one expansible member or a positioning lumen suitable for use in a surgical procedure. The distensible member 17 may be, but is not limited to, distension by air, gas, liquid, or any other suitable expansion element for use in a surgical procedure. The expansible member comprises of a front 17A and a back 17B. The back of the expansible member 17B may abut against a vessel wall 12. The front of the expansible member 17A may abut against a surgical component 16, such as a prosthetic graft, which forms a compression site 22. The front of the expansible member 17A abutting against the surgical component 16 urges the surgical component 16 against the vessel wall 12.

Figure 2:
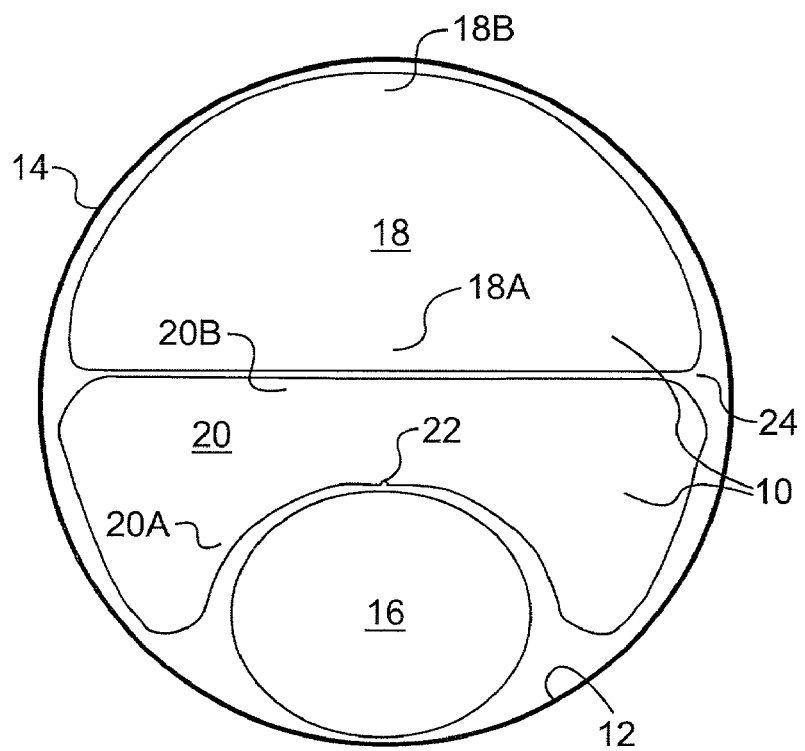
FIG. 2 is a transverse view of another embodiment of the present invention with a flat interface within a vessel.

In another embodiment illustrated in FIG. 2, the positioning apparatus 10 located within a vessel 14 comprises a delivery assembly (not shown in FIG. 2) and a distensible member comprising of a first expansible member 18 and a second expansible member 20. The expansible members may be inserted, or delivered, and distended. The order or degree of insertion and distension is not limited. The first expansible member 18 comprises a front 18A and a back 18B. The back of the first distended expansible member 18B abuts against a vessel wall 12. The second expansible member 20 also comprises of a front 20A and a back 20B. The front of the second distended expansible member 20A abuts against a surgical component 16, which urges the component against the vessel wall 12. The front of the second distended expansible member 20A abutting against the surgical component 16 may form a compression site 22.

The expansible member's location and size may be increased or decreased such that the surgical component 16 abuts against the vessel wall 12 allowing for manipulations of the surgical component 16. Additionally, the front of the first expansible member 18A and the back of the second expansible member 20B may contact forming a flat interface 24, as depicted in FIG. 2. The expansible members 18, 20 may be comprised of any suitable material for use during a surgical procedure.

Thus, the positioning apparatus 10 provides a surface that may be relocated and varied in size based on the distension of the expansible members. The positioning apparatus 10 allows for the movement of an object as illustrated, such as a surgical component 16, for further manipulations.

Figure 3:
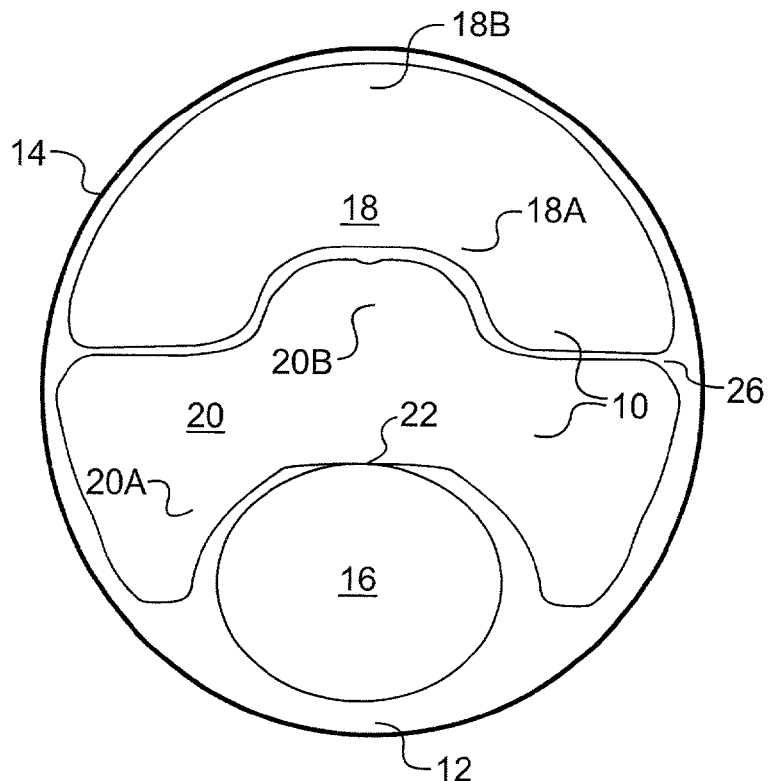
FIG. 3 is a transverse view of another embodiment of the present invention with a grooved interface within a vessel.
Figure 4:
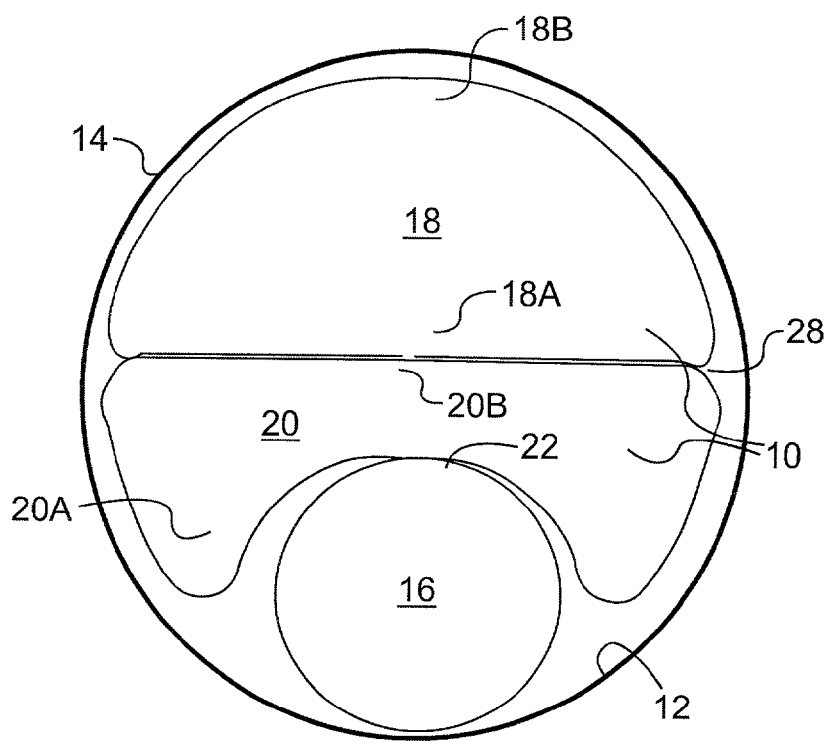
FIG. 4 is a transverse view of another embodiment of the present invention with an attachment interface within a vessel.

In another embodiment exemplified in FIG. 3, the contact between the front of the first expansible member 18A and the back of the second expansible member 20B forms a grooved interface 26. The present invention contemplates a variety of differently shaped first and second expansible members that take advantage of an inter-relationship between the front of the first expansible member 18A and the back of the second expansible member 20B when distended, such as, but not limited to, a male-female relationship, or any other suitable relationship. According to another embodiment of the invention as illustrated in FIG. 4, the contact between the front of the first expansible member 18A and the back of the second expansible member 20B forms an attached interface 28.

Figure 5:
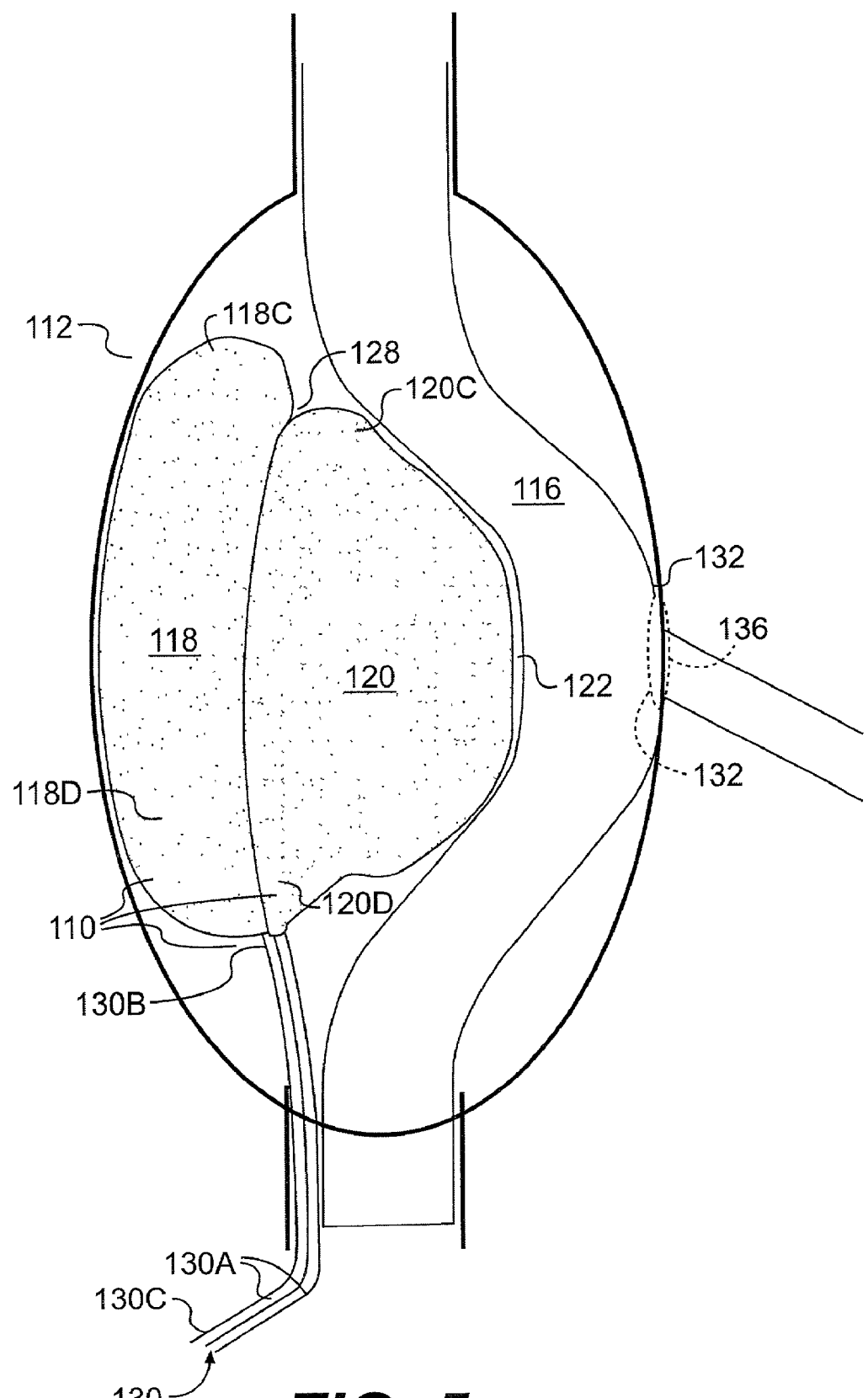
FIG. 5 is a longitudinal view of an embodiment of the present invention with an attachment interface within an aneurysm in a vessel.

FIG. 5 is a longitudinal cut of an aneurysm 112 illustrating an embodiment of a positioning apparatus 110, in accordance with the present invention. The positioning apparatus 110 may be inserted and distended. The order or degree of insertion and distension is not limited. The positioning apparatus 110 comprises a delivery assembly 130 and a distensible member having a first 118 and a second 120 expansible member. The delivery assembly 130 may have a plurality of chambers 130A with a first end 130B and a second end 130C. The first expansible member 118 may comprise a distal end 118C and a proximal end 118D, and a back (not illustrated in FIG. 5) and a front (not illustrated in FIG. 5). The second expansible member 120 may comprise a distal end 120C and a proximal end 120D, and a front (not illustrated in FIG. 5) and a back (not illustrated in FIG. 5). Each chamber 130A of the delivery assembly is interposed with the proximal ends of the first 118D and second 120D expansible members.

Additionally, the front of the first expansible member and the back of the second expansible member may interpose to form an attachment site 128. The front of the second expansible member may interpose with the surgical component 116 to form a compression site 122. The front of the second expansible member may also be incorporated or attached to the surgical component 116, forming an interconnection.

The distension of the expansible members may be commensurate with the alignment of a surgical component 116 such that the surgical component 116 interfaces with a vessel wall having an attachment of a branching artery 136. Thus, the surgical component 116 may be maneuvered to align with the vessel wall having the attachment of a branching artery 136 for the position and location of a plurality of sutures and/or fasteners 132 or any other appropriate fastening apparatus ensuring the attachment of the surgical component 116 to the vessel.

Specifically, the use of the positioning apparatus may allow internal bypass of a thoracic aneurysm without a need for an open operation or the need to occlude the thoracic aorta for any significant period of time to accommodate a repair.

It will be apparent to those skilled in the art that various modifications and variations can be made in the construction and configuration of the present invention, without departing from the scope or spirit of the invention. For instance, the distensible member arrangement may provide a surface that can be moved and whose size can be increased or decreased so that an object within an aorta or aortic aneurysm can be maneuvered into a position where further manipulations of the object can be employed. Specifically, the expansible members can be used to maneuver a prosthetic aortic graft anteriorly or posteriorly so as to allow the graft to be attached around the orificies of branching arteries whose flow is essential to the function of critical organs, such as the spinal cord or intestines. An advantage of such a system is that it may allow internal bypass of a thoracic aneurysm without the need for an open operation or the need to occlude the aorta for any significant period while the repair is being accomplished.

In addition, one or more expansible members could also be incorporated or attached to the wall of a surgical component. Furthermore, any number of expansible members could be included in the positioning apparatus for manipulation of a surgical component within a vessel.

It will be apparent to those skilled in the art that various modifications and variations can be made in the construction and configuration of the present invention, without departing from the scope or spirit of the invention. Thus, it is intended that the present invention cover the modifications and variations of the invention, provided they come within the scope of the appended claims and their equivalents.

What is claimed is:

1. A positioning apparatus for maneuvering a surgical component in a vessel having a vessel wall during a surgical procedure, said positioning apparatus comprising:
   the surgical component
   a delivery assembly having first and second chambers;
   a distensible member having a first and a second expansible member, said first expansible member having a distal end and a proximal end and a front and a back wherein said proximal end is interposed with the first chamber of said delivery assembly and the back is adapted to be abutted against the vessel wall, the second expansible member having a distal end and a proximal end and a front and a back wherein said proximal end is interposed with the second chamber of said delivery assembly and the front is abutted against said surgical component; and
   wherein said first and second expansible members are distended, and
   wherein said second expansible member is disposed between the surgical component and said first expansible member.

2. The positioning apparatus according to claim 1, wherein said second expansible member is interfaced with said surgical component during said surgical procedure.

3. The positioning apparatus according to claim 2, wherein said second expansible member is interfaced with said surgical component in the form of an interconnection.

4. The positioning apparatus according to claim 2, wherein said second expansible member is interfaced with said surgical component in the form of a compression site.

5. The positioning apparatus according to claim 1, wherein said first expansible member is in contact with said second expansible member forming an interface.

6. The positioning apparatus according to claim 5, wherein said interface is flat.

7. The positioning apparatus according to claim 5, wherein said interface is grooved.

8. The positioning apparatus according to claim 5, wherein said interface is an attachment.

9. A method of positioning a surgical component in a vessel having a vessel wall, comprising the steps of:
   delivering a positioning apparatus to a surgical site;
   distending at least one expansible member of the positioning apparatus such that the at least one expansible member abuts the surgical component and is disposed between the surgical component and the vessel wall; and
   maneuvering the position of the surgical component with the positioning apparatus to align the surgical component with a vessel wall having an attachment of a branching artery and,
   attaching the surgical component to the vessel wall around an orifice of the branching artery.

* * * * *